United States Patent [19]
Muller

[11] Patent Number: 5,830,208
[45] Date of Patent: Nov. 3, 1998

[54] PELTIER COOLED APPARATUS AND METHODS FOR DERMATOLOGICAL TREATMENT

[75] Inventor: David F. Muller, Boston, Mass.

[73] Assignee: LaserLite, LLC, Boston, Mass.

[21] Appl. No.: 791,608

[22] Filed: Jan. 31, 1997

[51] Int. Cl.[6] .............................. A61B 17/38; A61F 7/00; A61N 5/06
[52] U.S. Cl. .................................. 606/9; 606/20; 606/13
[58] Field of Search .................................. 606/9, 10, 11, 606/12, 20, 21, 22, 23, 28, 29, 31, 42

[56] References Cited

U.S. PATENT DOCUMENTS

| | | |
|---|---|---|
| 4,015,591 | 4/1977 | Suzuki et al. . |
| 4,483,341 | 11/1984 | Witteles .................................. 606/21 |
| 4,614,191 | 9/1986 | Perler .................................. 128/399 |
| 4,832,024 | 5/1989 | Boussignac et al. . |
| 4,860,744 | 8/1989 | Johnson et al. . |
| 4,962,761 | 10/1990 | Golden .................................. 128/400 |
| 5,007,433 | 4/1991 | Hermsdörffer et al. ................. 128/742 |
| 5,057,104 | 10/1991 | Chess .................................. 606/9 |
| 5,075,555 | 12/1991 | Woldseth et al. .................. 250/370.15 |
| 5,097,828 | 3/1992 | Deutsch .................................. 128/399 |
| 5,125,923 | 6/1992 | Tanner et al. .............................. 606/10 |
| 5,143,080 | 9/1992 | York .......................................... 128/736 |
| 5,169,384 | 12/1992 | Bosniak et al. .......................... 604/20 |
| 5,207,227 | 5/1993 | Powers .................................... 128/691 |
| 5,207,674 | 5/1993 | Hamilton ................................. 606/20 |
| 5,241,965 | 9/1993 | Mick ....................................... 128/713 |
| 5,282,797 | 2/1994 | Chess ......................................... 606/9 |
| 5,314,423 | 5/1994 | Seney ........................................ 606/20 |
| 5,334,191 | 8/1994 | Poppas et al. ............................. 606/12 |
| 5,344,418 | 9/1994 | Ghaffari ...................................... 606/9 |
| 5,372,124 | 12/1994 | Takayama et al. ......................... 128/4 |
| 5,405,368 | 4/1995 | Eckhouse ................................. 607/88 |
| 5,486,172 | 1/1996 | Chess ........................................ 606/20 |
| 5,529,067 | 6/1996 | Larsen et al. ............................ 128/642 |
| 5,616,139 | 4/1997 | Okamoto ..................................... 606/4 |

OTHER PUBLICATIONS

*New Device Lessens the Pain Associated with Laser Therapy*, L. Sabbagh, Dermatology Times, Sep. 1996, two pages.

Primary Examiner—Jennifer Bahr
Assistant Examiner—Sonya Harris-Ogugua
Attorney, Agent, or Firm—Nutter, McClennen & Fish, LLP

[57] ABSTRACT

An apparatus for treating dermatological conditions with radiation includes a Peltier device for cooling the treatment area of the patient's skin. The Peltier cooling device has a cold surface in thermal communication with the treatment area and a hot surface, with an aperture extending between the cold and hot surfaces through which radiation is directed to the treatment area. In one embodiment, a lens disposed within the aperture of the cooling device distributes the cooling effect to provide substantially uniform cooling across the treatment area. A temperature sensor senses the temperature of the treatment area and is used to control the Peltier cooling device and/or the radiation source to ensure that the treatment area does not exceed a predetermined temperature. Various radiation sources are suitable for use with the Peltier cooled apparatus, including lasers and gas-discharge lamps, such as arc lamps and flash lamps.

25 Claims, 5 Drawing Sheets

PELTIER COOLED APPARATUS AND METHODS FOR DERMATOLOGICAL TREATMENT

CROSS REFERENCE TO RELATED APPLICATIONS

Not applicable.

STATEMENTS REGARDING FEDERALLY SPONSORED RESEARCH

Not applicable.

BACKGROUND OF THE INVENTION

The invention relates to apparatuses and methods for treating dermatological conditions and, more specifically, to cooling apparatuses and related methods for assisting the treatment of dermatological conditions.

Various techniques and associated devices are known for treating dermatological conditions such as cutaneous vascular disorders, including telangiectasia (spider capillaries), PortWine Stains and skin pigmentation irregularities. One such technique is referred to as sclerotherapy, in which chemical agents are intravascularly injected into the abnormal blood vessels. Another technique for treating such conditions is the application of electromagnetic energy to the affected area to destroy the abnormality with heat.

Illustrative radiation sources that have been used in such treatment apparatus include lasers, arc lamps and flash lamps. In U.S. Pat. No. 5,344,418 (Ghaffari), arc lamps are described as a suitable lower cost alternative to lasers since, in the treatment of vascular lesions, the coherence of the laser beam is not critical as long as a light source with proper power at the right wavelengths can be focused onto the skin.

According to U.S. Pat. No. 5,405,368 (Eckhouse), flash lamps are preferred due to the ability to control the depth of radiation penetration by adjusting the pulse width driving the flash lamp. Further, the relatively wide wavelength range of flash lamps is believed to facilitate their use for different types of skin treatments, as compared to lasers.

Treatment of subcutaneous vascular disorders with electromagnetic radiation results in absorption of energy by the overlying and surrounding epidermis. Conventional vascular treatment apparatus generally includes a cooling mechanism to reduce the risk of heat injury to the epidermis, such as permanent scaring. In particular, U.S. Pat. No. 5,057,104 (Chess) describes different mechanisms for cooling the epidermis during laser treatment, including the use of a coolant gas and a cooling fluid.

SUMMARY OF THE INVENTION

The present invention relates to Peltier cooled apparatuses and related methods for treating dermatological conditions. A Peltier device is used to cool an area of the patient's epidermis targeted for treatment with radiation. The Peltier device has an aperture extending between a cold surface in thermal communication with the patient's epidermis and a hot surface, with the aperture defining the treatment area. A radiation source is positioned in substantial vertical alignment with the aperture of the cooling device to permit the treatment area to be irradiated through the aperture. With this arrangement, the treatment area is cooled by the Peltier devices during irradiation.

In one embodiment, a lens is disposed in the aperture of the Peltier device and in contact with the treatment area to distribute the cooling effect provided by the Peltier device so as to uniformly cool the treatment area without interfering with the radiation. To this end, the lens is comprised of a material that is at least substantially transparent to light and which has good thermal conductivity characteristics. Suitable lens materials include quartz, sapphire and diamond. The lens may additionally serve to focus the radiation onto the treatment area. Depending on the type of radiation source used to irradiate the treatment area and the type of treatment performed, an optical filter may be disposed within the aperture of the Peltier device in order to optimize the wavelength of light irradiating the treatment area. Further thermal coupling advantages may be achieved with the use of a thermally conductive material between the lens and epidermis.

A temperature sensor senses the temperature of the treatment area and generates a temperature output signal indicative of the treatment area temperature. One or both of the Peltier cooling device and the radiation source may be controlled in response to the temperature output signal. In this way, damage to the treatment area and/or surrounding skin can be minimized by ensuring that the skin temperature does not exceed a predetermined temperature. Control of the Peltier cooling device and/or the radiation source may be pre-programmed so as to follow a predetermined sequence and timing of activation and de-activation steps.

A heat dissipation mechanism prevents the Peltier device from overheating. In one embodiment, a heat sink is provided in thermal communication with the hot surface of the Peltier cooling device. The heat sink has an aperture aligned with the aperture of the cooling device through which radiation from the radiation source is directed toward the treatment area. In another embodiment, a cooling gas is passed over the hot surface of the Peltier device. Alternatively however, a cooling liquid may be used to cool the Peltier device.

Various types of radiation sources are suitable for use with the Peltier cooled dermatological treatment apparatus described herein. In particular, the radiation source may be a coherent laser light source or an incoherent light source, such as a gas-discharge lamp. Suitable types of gas-discharge lamps include flash lamps and arc lamps. The choice of radiation source will depend on such factors as cost, treatment type, desired depth of skin penetration (which is a function of wavelength, among other things), and control scheme. In one embodiment, a pulsed flash lamp radiation source is controlled by the temperature output signal so as to terminate further pulsing when the temperature output signal indicates that the temperature of the treatment area has reached a predetermined level.

DETAILED DESCRIPTION OF THE INVENTION

Figure 1:
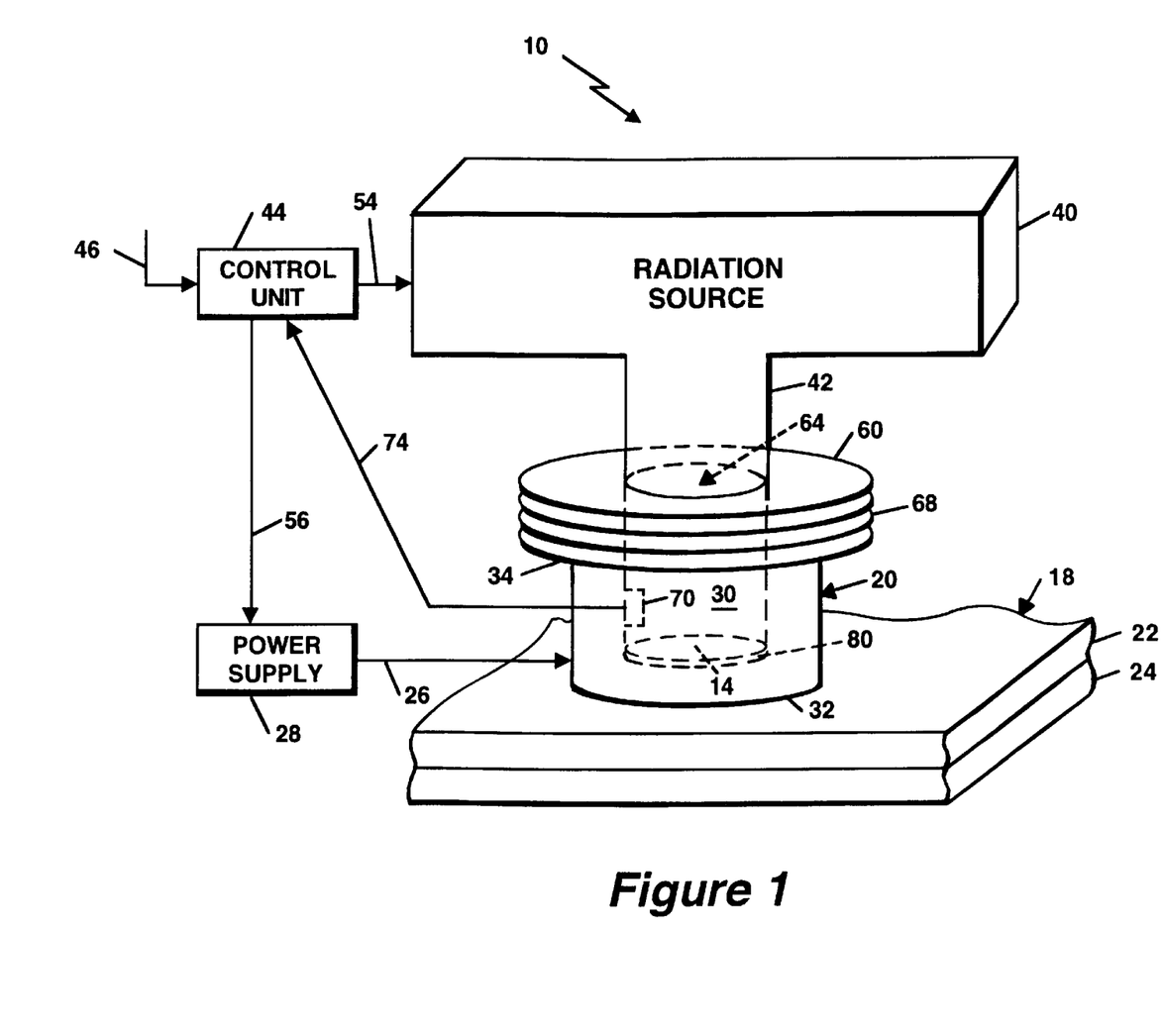
FIG. 1 is a perspective view of Peltier cooled apparatus for treating dermatological conditions according to the invention.

Referring to FIG. 1, an apparatus 10 for treating certain dermatological conditions with radiation includes a Peltier cooling device 20 for cooling an area 14 of a patient's skin 18 targeted for treatment by a radiation source 40. Although the apparatus 10 is positioned over the epidermal layer 22, it may be intended for treating conditions of a subcutaneous layer 24.

Peltier cooling devices which operate in accordance with the Peltier effect are well known. In such devices, current flow between dissimilar conductive materials results in heat being absorbed at one side 32 (i.e., "the cold surface") of the device and heat being generated at the other side 34 (i.e., "the hot surface") of the device, with the cold surface and hot surface being determined by the direction of current flow. A power supply 28 supplies current to the Peltier device 20 via a signal line 26.

In the illustrative embodiment, the Peltier device 20 is a semiconductor device in which the dissimilar materials are semiconductor materials, thereby effectively providing a solid state heat pump. Typical semiconductor materials having suitable thermoelectric properties for use in the device 20 include bismuth telluride.

The Peltier device 20 has an aperture 30 extending therethrough from the cold surface 32 positioned in thermal communication with the patient's skin 18 and the hot surface 34. More particularly, thermal communication between the cold surface 32 of the device 20 and the patient's skin may be achieved by providing the cold surface 32 in direct contact with the patient's skin or alternatively, through indirect contact via a lens and/or a suitable thermally conductive material, such as a gel. The aperture 30 defines the treatment area 14 and permits radiation from a source 40 to be delivered through it to the treatment area 14. While the aperture 30 in the illustrative embodiment is substantially circular in shape, the shape of the aperture 30 through the Peltier cooling device 20 can be readily varied in order to facilitate manufacture of the device and/or to optimize definition of the treatment area. For example, where the apparatus 10 is intended to treat a relatively large skin area and/or an area of a particular shape, it may be advantageous to enlarge the aperture 30 and/or to modify the shape of the aperture 30 so as to tailor its shape to the shape of the anticipated treatment area 14. Furthermore, the overall shape and size of the Peltier device 20 which, in the illustrative embodiment is cylindrical, can be varied. It will be appreciated that by varying the shape and size of the device, the area of the cold surface 32 can be varied, thereby affecting the extent of cooling.

A heat sink 60 is optionally provided to direct heat away from the device 20 and the adjacent treatment area 14. In the illustrative embodiment, the heat sink 60 is disposed in thermal communication with the hot surface 34 of the device 20 and includes an aperture 64 in substantial vertical alignment with the aperture 30 of cooling device in order to permit light from radiation source 40 to be directed to the treatment area 14. It will appreciated that the heat sink 60 may take various forms in terms of its size, shape and design, and the particular arrangement of fins 68. Furthermore, alternative mechanisms, such as a cooling liquid or gas, may be used to disperse heat from the hot surface 34 of the Peltier cooling device 20. As one example, a cooling gas is used in the embodiment of FIG. 3 to dissipate heat from the hot surface of the Peltier device.

Figure 2:
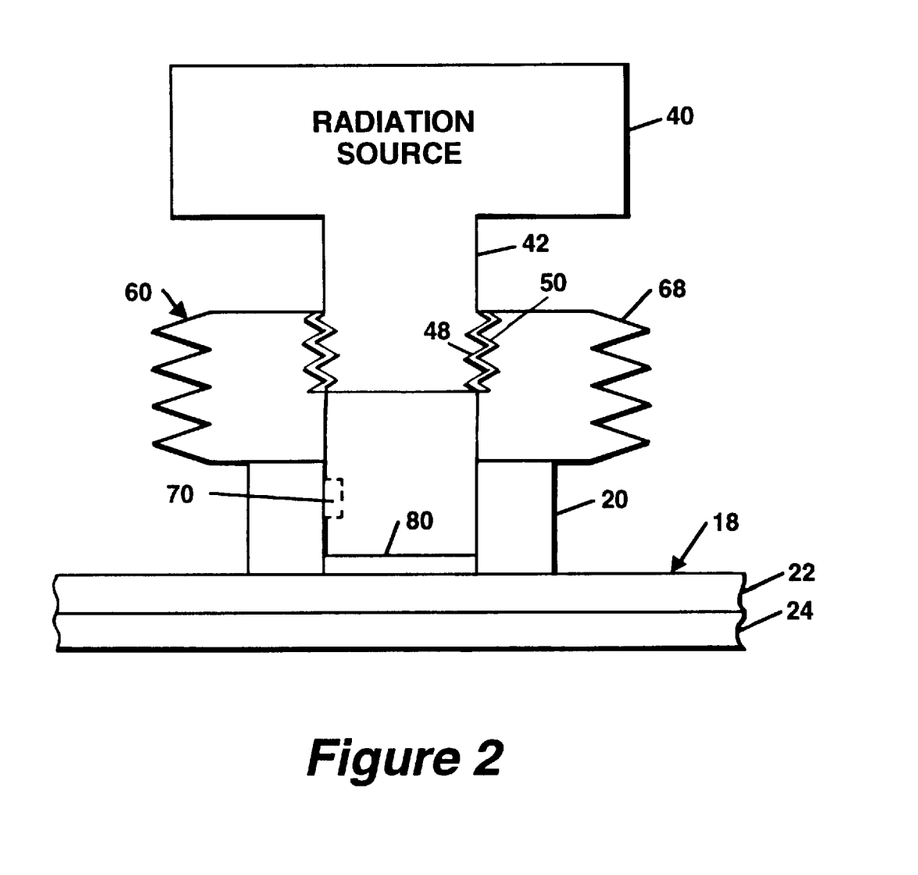
FIG. 2 is a cross-sectional view of the apparatus of FIG. 1.

Referring also to FIG. 2, in which like numbers refer to like elements, a cross-sectional view of the apparatus 10 is shown without a control unit 44 and power supply 28 for simplicity of illustration. Various ways of thermally and mechanically coupling the radiation source 40, heat sink 68 and Peltier cooling device 20 are possible. In the illustrative embodiment, the aperture 64 of the heat sink 60 has threads 50 and an outer surface 42 of the radiation source 40 has complementary threads 48 adapted for mating with the threads of the heat sink 60, thereby affecting mechanical coupling of the radiation source 40 and the heat sink 60. The heat sink 60 is coupled to the Peltier cooling device 20 with a thermally conductive epoxy.

Various types of radiation sources 40 are suitable for use with the dermatological treatment apparatus 10. Illustrative of such sources are coherent laser sources and incoherent gas-discharge sources. Factors such as cost, the intended application of the apparatus and the control scheme dictate the type of radiation source used. For example, gas-discharge lamps are generally less expensive than laser sources. Also, the relatively wide range of wavelengths associated with flash lamps make them advantageous for use in apparatuses for treating a variety of skin conditions requiring different depths of radiation penetration. Furthermore, the pulsed nature of light provided by a flash lamp is conducive to pulse width control as a way of controlling light intensity. Suitable lasers for providing the radiation source 40 include $CO_2$, holmium, Er:YAG, Nd:YAG and flash lamp pumped dye lasers.

A control unit 44 controls activation and de-activation of the radiation source 40 via a control signal line 54 and of the power supply 28 via a control signal line 56. More particularly, the control unit 44 controls the amount and timing of radiation provided by the source 40 to the treatment area 14 as well as the amount and timing of current provided by the power supply 28 to the Peltier cooling device 20, thereby controlling the extent and timing of cooling. Control unit 44 is responsive to various factors, including external control by the operator of the apparatus via an input signal line 46. Additionally, control unit 44 may be responsive to a temperature output signal 74 provided by a temperature sensor 70 for controlling one or both of the radiation source 40 and the power supply 28. Further, the control unit 44 may be pre-programmed to control the Peltier cooling device 20 and/or the radiation source 40 so as to follow a predetermined sequence and timing of activation and de-activation steps. For example, the radiation source 40 may be activated a predetermined duration after activation of the Peltier cooling device and provide a predetermined number of light pulses prior to being de-activated for a further predetermined duration.

Temperature sensor 70 senses the temperature of the treatment area 14 and provides an output signal 74 indicative of such temperature. It will appreciated by those of ordinary skill in the art that the temperature sensor 70 may take various forms and may be located at various positions relative to the apparatus 10 and treatment area 14. In the illustrative embodiment, the temperature sensor 70 is a thermocouple disposed within the aperture 30 of the cooling device 20. Since the temperature sensor 70 may not directly to contact the treatment area 14, as in the illustrative embodiment, the temperature output signal 74 is used to infer the temperature of the treatment area 14.

The control unit 44 is responsive to the temperature output signal 74 for deactivating the radiation source 40 when the temperature of the treatment area 14 reaches a predetermined level, as will be described further in conjunction with FIG. 5. In this way, the temperature sensor 70 and the temperature output signal 74, which is fed back to the control unit, ensure that the treatment area remains at a safe temperature.

A lens 80 is disposed in the aperture 30 of the Peltier device 20 and, in use, contacts the treatment area 14. More particularly, the lens is substantially flush with the cold surface 32 of the device. A thermally conductive material, such as a gel, may be disposed between the cold surface 32, lens 80 and the treatment area 14 in order to enhance the cooling of the skin.

The lens 80 distributes the cooling effect provided by the Peltier device, so as to substantially uniformly cool the treatment area 14. The lens 80 is at least substantially transparent to light to prevent interference with irradiation of the treatment area 14. Exemplary materials having suitable light transparency and thermal conductivity characteristics for providing the lens 80 include quartz, diamond and sapphire. The lens 80 can be a zero power lens and may be provided with optical characteristics for focusing light from the source 40 onto the treatment area 14.

The illustrative lens 80 has a diameter substantially equal to the diameter of the aperture 30 and is coupled to the cooling device 20 with a thermally conductive epoxy. Alternatively, the lens 80 may extend beyond the diameter of the aperture 30 into a notch (not shown) in the cold surface 32 of the device 20 in order to increase the thermal coupling between the device 20 and the lens 80 by increasing the surface area of the lens in contact with the cold surface 32.

It is contemplated that the apparatus 10 will be moved to different treatment areas of the patient during a treatment procedure. In a preferred embodiment, the cooling device 20, heat sink 60 and radiation source 40 are arranged to form a lightweight hand-held unit in order to facilitate placement and movement of the apparatus. Due to the added size and weight, the control unit 44 and power supply 28 may be provided as a separate stationary unit, with flexible electrical cabling carrying signal lines 74 and 26 coupling the stationary and hand-held units.

Figure 3:
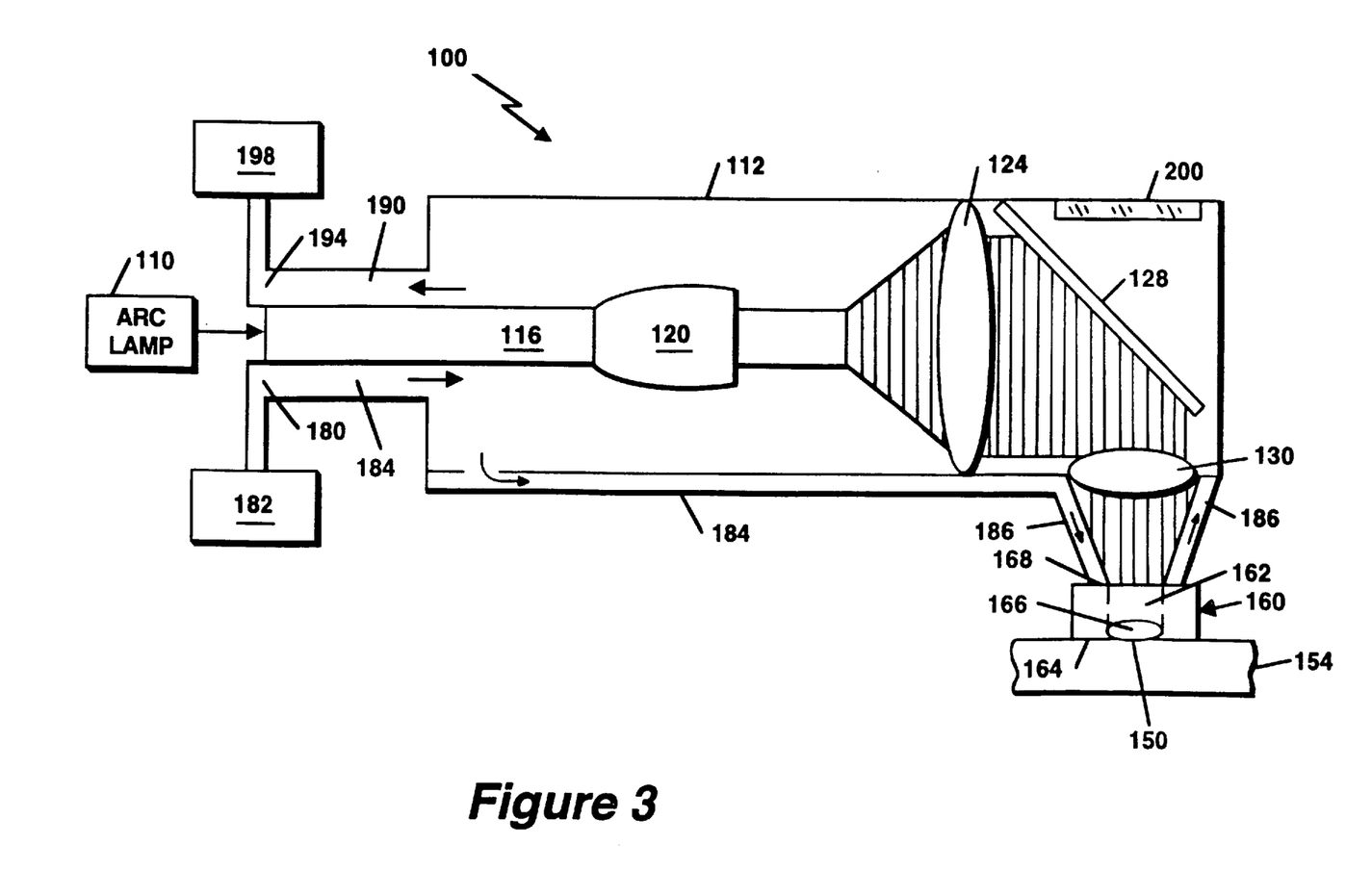
FIG. 3 shows an alternate embodiment of Peltier cooled apparatus for treating dermatological conditions in which the radiation source is an arc lamp.

Referring to FIG. 3, an alternate embodiment 100 includes an arc lamp radiation source 110 and a Peltier cooling device 160 for cooling a treatment area 150 of a patient's skin 154 during irradiation by radiation source 110. The Peltier cooling device 160 is substantially identical to the device 20 of FIGS. 1 and 2. Thus, the Peltier cooling device 160 has an aperture 162 extending from a cold surface 164 to a hot surface 168, as shown. A lens 166 disposed in the aperture 162 disperses the cooling so as to substantially uniformly cool the treatment area 150. Unlike the Peltier cooling device 20 of FIGS. 1 and 2 however, device 160 is not cooled by a heat sink. Rather, the device 160 is cooled by a gas flowing through a housing 112 and past the hot surface 168 of the device, as will be described. For simplicity of illustration, certain features are omitted from FIG. 3, including the control unit, power supply and temperature sensor.

A fiber optic cable 116 disposed in the housing 112 couples light from the arc lamp 110 to the treatment area 150. More particularly, the fiber optic cable 116 is coupled to a fiber terminator 120 which directs light from the cable toward a primary lens 124. Light which passes through the primary lens 124 is reflected by a dichroic mirror 128 toward a secondary mirror 130 and light passing through the secondary mirror 130 is directed toward the treatment area 150. More particularly, light passing through the secondary mirror 130 is directed through the aperture 162 in the Peltier cooling device 160.

The housing 112 includes a coolant input port 180 through which cooling gas from a reservoir 182 is directed. The gas thus introduced into the housing 112 is directed through an input passage 184 and flows past the hot surface 168 of the Peltier cooling device 160 via passages 186. The cooling gas exits the apparatus 100 through an output passage 190 and coolant output port 194 to a reservoir 198. Suitable gas coolants include nitrogen, helium and carbon dioxide. It will be appreciated, however, that the apparatus 110 can be readily modified to accommodate a cooling liquid through the passages described above in order to cool the Peltier device 160. A viewing window 200 may be provided through an upper surface of the housing 112 in order to permit the treatment area 150 to be observed during treatment.

Figure 4:
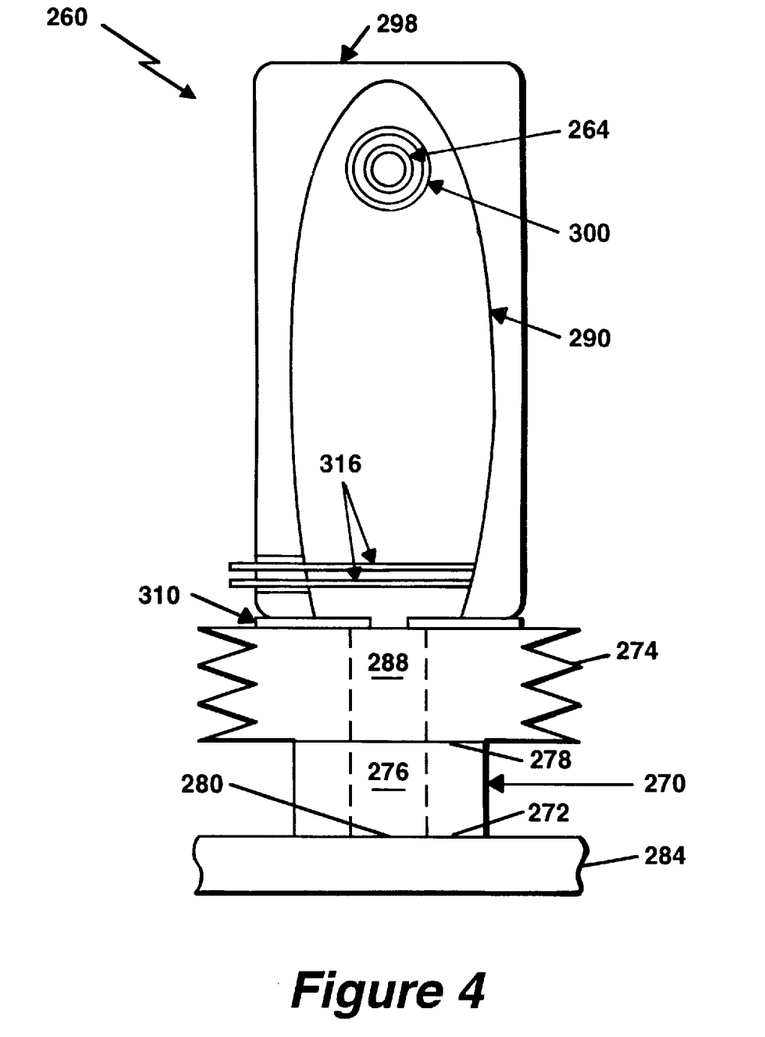
FIG. 4 shows another alternate embodiment of Peltier cooled apparatus for treating dermatological conditions in which the radiation source is a flash lamp.

Referring also to FIG. 4, a further embodiment 260 of the invention includes a flash lamp radiation source 264 and a Peltier cooling device 270 for cooling the treatment area 280 of a patient's skin during irradiation by the flash lamp 264. The Peltier cooling device 270 is substantially identical to device 20 in FIG. 1 and is adapted for coupling to a heat sink 274 which is substantially identical to heat sink 60 of FIG. 1. Thus, Peltier device 270 has an aperture 276 extending from a cold surface 272 to a hot surface 278 thereof through which radiation from the flash lamp 264 is directed toward a treatment area 280 of a patient's skin 284 in use. The heat sink 274 has an aperture 288 extending therethrough in substantial vertical alignment with the aperture 276 of the Peltier device 270, as shown. Certain elements, including the control unit, power supply and temperature sensor, are omitted from FIG. 4 for simplicity of illustration.

In the illustrative embodiment, the flash lamp 264 is disposed in a reflector 290 within a housing 298. The reflector 290 has a high reflectivity in the visible and ultraviolet spectral range and may be comprised of a metallic material, such as polished aluminum. The exemplary reflector 290 is elliptical, with the flash lamp 264 being positioned at a first focal point of the ellipse and the treatment area 280 being disposed at the other focal point. Other reflector shapes, such as parabolic or circular, are also suitable. Furthermore, the flash lamp 264 may be used without a reflector, with sufficient treatment energy density being achieved by locating the flash lamp in close proximity to the treatment area 280.

A glass tube 300 may be disposed concentrically around the flash lamp 264 for optimizing the energy efficiency of the lamp 264. More particularly, the glass tube 300 has a fluorescent material deposited on it which absorbs the UV portion of the spectrum so that the wavelength of light emitted from the flash lamp 264 is optimized for absorption in the blood, such as between about 500 and 600 nanometers.

A collimator or iris 310 is disposed between the housing 298 and the heat sink 274 in order to further control the length and width of the treatment area 280. That is, while the aperture 278 through the Peltier device defines the treatment area 280, the irradiated area can be further narrowed by adjustable collimator 310. An optional pair of filters 316 may be mounted in the housing 298 to control the spectrum and intensity of light provided by the flash lamp 264. In particular, the bandwidth of the filters 316 is tailored for particular applications since the penetration depth of the light is a function of its wavelength in addition to other factors such as scattering by the skin 284 and thermal properties of the skin.

Figure 5:
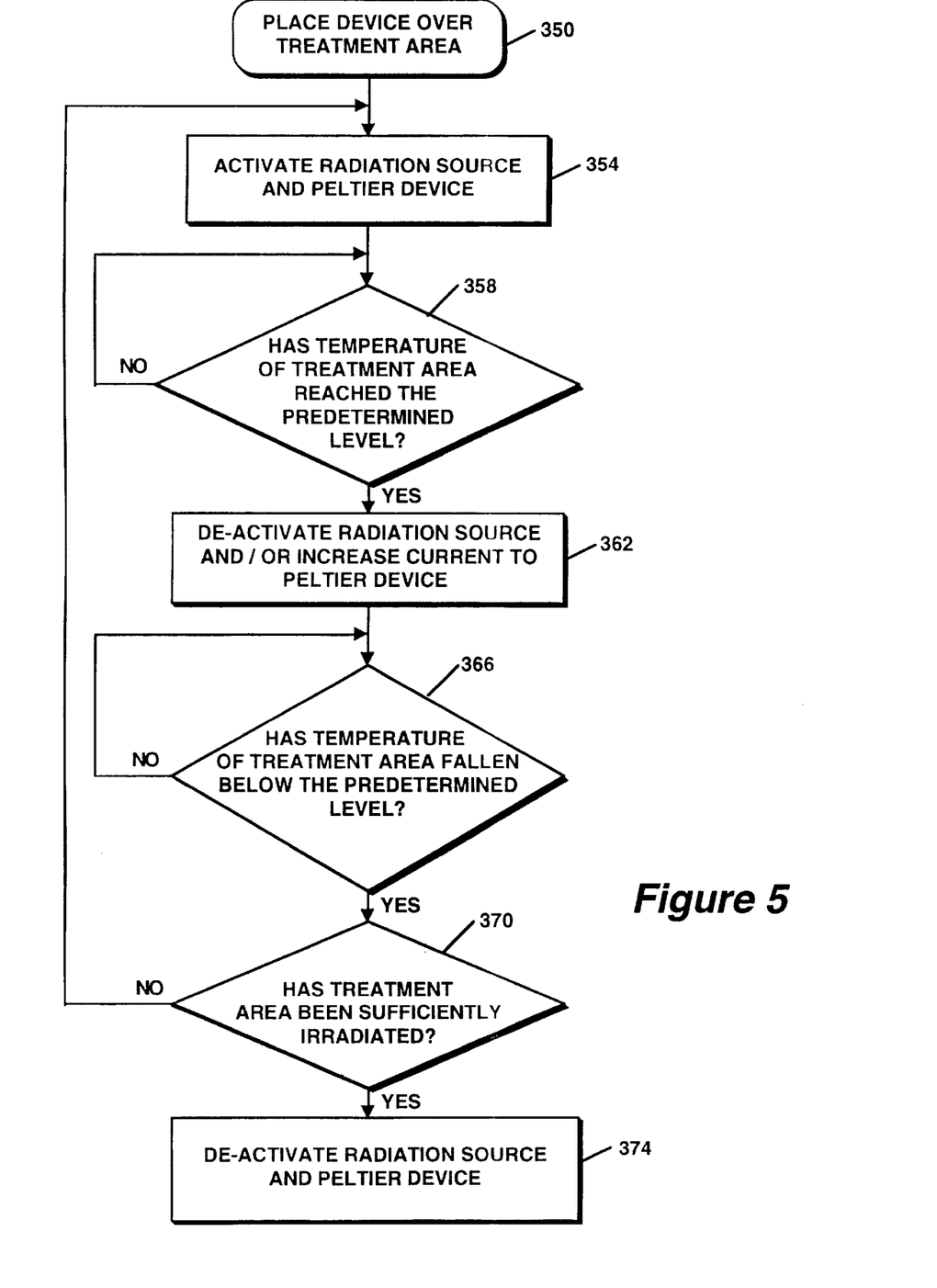
FIG. 5 is a flow diagram illustrating a method of use of the Peltier cooled apparatuses described herein.

Referring also to FIG. 5, an illustrative method of use of the Peltier cooled apparatuses of FIGS. 1–4 will be described with particular reference to treatment with the apparatus of FIGS. 1 and 2. Treatment is commenced in step 350, by placing the apparatus 10 over the treatment area 14, with the aperture 30 in the Peltier cooling device 20 vertically aligned with the treatment area 14. This step may be facilitated by observing the treatment area 14 through a viewing window of the type shown in FIG. 3 for example. step 354, in response to actuation by the user via input signal line 46 (FIG. 1), the control unit 44 activates the radiation source via control signal line 54 and the power supply 28 via signal line 56. Upon activation, the radiation source 40 irradiates the treatment area 14 through the heat sink aperture 64 and the Peltier device aperture 30. The parameters of the light provided by the radiation source 40 (e.g., wavelength, intensity and duration) will vary depending on the type of treatment and the type of source. Activation of the power supply 28 causes current to be supplied to the Peltier cooling device 20. The amount of current provided to the device 20 is a function of the device specifications and the extent of cooling desired. It will be appreciated that activation of the radiation source 40 and the Peltier device 20 may or may not occur simultaneously. For example, generally, it is desirable to "pre-cool" the patient's skin by activating the Peltier device 20 prior to irradiation by the source 40 in order to improve the efficacy of the cooling provided by the device 20.

Thereafter, it is determined, in step 358, whether the temperature of the treatment area 14 has reached a predetermined level. This step is achieved by the control unit 44 monitoring the temperature output signal 74 from the temperature sensor 70. Preferably, the predetermined temperature level is a few degrees below a "safe" skin temperature in order to avoid skin injury. With this arrangement, the propagation delay associated with "feeding back" the temperature output signal 74 to the control unit 44 is taken into account. That is, if the skin temperature is rising, by the time it reaches an unsafe temperature, the control unit 44 will have sensed that the temperature has reached the predetermined level and taken action to prevent skin damage accordingly.

In the event that it is determined in step 358 that the temperature has reached the predetermined level, then step 362 is next performed, in which the radiation source 40 is de-activated. Alternatively or additionally, the level of current provided by the power supply 28 to the Peltier cooling device 20 may be increased so as to increase the extent of cooling supplied by the device. If however, the temperature of the treatment area 14 has not reached the predetermined level, then monitoring step 358 is repeated, so as to continue monitoring the skin temperature.

Following step 362, it is determined, in step 366, whether the temperature of the treatment area 14 has fallen below the predetermined level. If the temperature has not fallen below the predetermined level, then step 366 is repeated until the temperature has fallen to the predetermined level. It will be appreciated by those of ordinary skill in the art that "hysteresis" may be provided in the system by determining in step 366 whether the treatment area temperature has fallen below a second predetermined level which is lower than the first predetermined level. In this way, the skin is cooled to a temperature lower than the "safe" temperature level prior to continuing treatment.

Once the treatment area temperature has fallen below the predetermined level, then it is next determined in step 370, whether the treatment area has been sufficiently irradiated. This determination can be facilitated with the use of a viewing window, like that shown in FIG. 3. If the treatment area 14 has not been sufficiently irradiated, then treatment is continued by repeating step 354, as shown. If it is determined in step 370 that the treatment area has been sufficiently irradiated, then treatment is thereafter terminated in step 374 by de-activating the radiation source 40 and the Peltier cooling device 20. It will be appreciated that the relative timing of the de-activation can be varied to suit a particular application. For example, it may be desirable to first deactivate the radiation source 40 and continue cooling the treatment area with the Peltier device 20 for some duration thereafter, depending, for example, on the anticipated time constant associated with heat dissipation from the skin.

The foregoing description of the illustrative embodiments of the invention is presented to indicate the range of constructions to which the invention applies. Variations in the physical architecture and dimensions of the invention will be apparent to those having ordinary skill in the art based upon the disclosure herein, and such variations are considered to be within the scope of the invention in which patent rights are asserted, as set forth in the claims appended hereto. All publications and references cited herein are expressly incorporated herein by reference in their entirety.

What is claimed is:

1. An apparatus for treating dermatological conditions comprising:

a radiation source for irradiating a treatment area of a patient's skin; and a Peltier cooling device having a first surface adapted for being in thermal communication with the treatment area of the patient's skin, a second, opposite surface, and an aperture extending between the first and second surfaces and positioned to permit the radiation source to irradiate the treatment area of the patient's skin through the aperture, the Peltier cooling device being selectively operable to cool the treatment area of the patient's skin.

2. The apparatus of claim 1 wherein the Peltier cooling device is a semiconductor device.

3. The apparatus of claim 1 further comprising a temperature sensor for sensing the temperature of the treatment area of the patient's skin.

4. The apparatus of claim 3 wherein the temperature sensor provides a temperature output signal indicative of the temperature of the treatment area to a control unit that controls output from the radiation source in response to the temperature output signal.

5. The apparatus of claim 3 further comprising a pre-programmed control unit for controlling activation and de-activation of the radiation source and the Peltier cooling device in accordance with a predetermined sequence and timing.

6. The apparatus of claim 3 further comprising a lens in substantial vertical alignment with the aperture of the Peltier cooling device.

7. The apparatus of claim 6 wherein the lens has a surface adapted for being in contact with the patient's skin.

8. The apparatus of claim 7 wherein the lens is made of a thermally conductive, substantially optically transparent material selected from the group consisting of quartz, diamond and sapphire.

9. The apparatus of claim 3 further comprising an optical filter in substantial vertical alignment with the aperture of the Peltier cooling device.

10. The apparatus of claim 3 further comprising a heat sink in thermal communication with the second surface of the Peltier cooling device.

11. The apparatus of claim 1 wherein the radiation source is a laser.

12. The apparatus of claim 1 wherein the radiation source is a gas-discharge lamp.

13. The apparatus of claim 12 wherein the radiation source is a flash lamp.

14. The apparatus of claim 12 wherein the radiation source is an arc lamp.

15. An apparatus for treating dermatological conditions comprising:

a Peltier cooling element having a first surface in thermal communication with a treatment area of a patient's skin and a second, opposite surface distal from the treatment area of the patient's skin, wherein the Peltier cooling element has an aperture extending from the first surface to the second surface;

a light source in substantial vertical alignment with the aperture of the Peltier cooling element for irradiating the treatment area of the patient's skin;

a lens disposed in the aperture of the Peltier cooling element having a surface in contact with the treatment area; and a power source coupled to the Peltier cooling element for activating the Peltier cooling element to cool the treatment area of the patient's skin.

16. The apparatus of claim 15 wherein the lens is comprised of a material selected from the group consisting of quartz, diamond and sapphire.

17. The apparatus of claim 15 further comprising a heat sink in thermal communication with the second surface of the Peltier cooling element.

18. A method for treating dermatological conditions comprising the steps of:

providing a treatment apparatus having a radiation source and a skin cooling Peltier element having an aperture extending therethrough;

irradiating a treatment area of a patient's skin through the aperture of the Peltier element with radiation from the radiation source; and activating the Peltier element to cool the treatment area of the patient's skin.

19. An apparatus for treating dermatological condition comprising:

a radiation source for irradiating a treating area of a patient's skin; and a Peltier cooling device having a first surface, a second surface and an aperture extending between the first and second surfaces, wherein the Peltier cooling device is adapted to be disposed over the treatment area of the patient's skin with the aperture substantially vertically aligned with the treatment area and the radiation source positioned to irradiate the treatment area of the patient's skin through the aperture, wherein the treatment area of the patient's skin is cooled upon activation of the Peltier cooling device.

20. The apparatus of claim 19 further comprising a heat sink in thermal communication with the second surface of the Peltier cooling device.

21. The apparatus of claim 19 further comprising a cooling substance flowing over the second surface of the Peltier cooling device.

22. The apparatus of claim 21 wherein the cooling substance is a cooling liquid or a cooling gas.

23. An apparatus for treating dermatological conditions comprising:

a radiation source for irradiating a treatment area of a patient's skin;

a Peltier cooling device operable to cool the treatment area of the patient's skin and having a first surface in thermal communication with the treatment area of the patient's skin, a second, opposite surface and an aperture extending from the first surface to the second surface, wherein the radiation source is positioned for irradiating the treatment area of the patient's skin through the aperture; and a heat sink in thermal communication with the second surface of the Peltier cooling device.

24. An apparatus for treating dermatological conditions comprising:

a Peltier cooling element having a first surface in thermal communication with a treatment area of a patient's skin and a second, opposite surface distal from the treatment area of the patient's skin, wherein the Peltier cooling element has an aperture extending from the first surface to the second surface;

a light source in substantial vertical alignment with the aperture of the Peltier cooling element for irradiating the treatment area of the patient's skin;

a lens disposed in the aperture of the Peltier cooling element having a surface in contact with the treatment area;

a power source coupled to the Peltier cooling element for activating the Peltier cooling element to cool the treatment area of the patient's skin; and a heat sink in thermal communication with the second surface of the Peltier cooling element.

25. An apparatus for treating dermatological conditions comprising:

a radiation source for irradiating a treatment area of a patient's skin;

a Peltier cooling device having a first surface, a second surface and an aperture extending between the first and second surfaces, wherein the Peltier cooling device is adapted to be disposed over the treatment area of the patient's skin with the aperture substantially vertically aligned with the treatment area and the radiation source is positioned to irradiate the treatment area of the patient's skin through the aperture, wherein the treatment area of the patient's skin is cooled upon activation of the Peltier cooling device; and a heat sink in thermal communication with the second surface of the Peltier cooling device.

* * * * *

UNITED STATES PATENT AND TRADEMARK OFFICE
CERTIFICATE OF CORRECTION

PATENT NO. : 5,830,208
DATED : November 3, 1998
INVENTOR(S) : David F. Muller

It is certified that error appears in the above-indentified patent and that said Letters Patent is hereby corrected as shown below:

On line 1 of claim 19, replace "condition" with -- conditions --; and on line 3, replace "treating" with -- treatment --.

Signed and Sealed this

Fourth Day of January, 2000

Attest:

Attesting Officer

*Acting Commissioner of Patents and Trademarks*